(12) United States Patent
Sunshine (10) Patent No.: US 6,606,566 B1
(45) Date of Patent: Aug. 12, 2003

(54) COMPUTER CODE FOR PORTABLE SENSING

(76) Inventor: Steven A. Sunshine, 985 S. Oakland Ave., Pasadena, CA (US) 91106

( * ) Notice: Subject to any disclaimer, the term of this patent is extended or adjusted under 35 U.S.C. 154(b) by 31 days.

(21) Appl. No.: 09/703,467

(22) Filed: Oct. 31, 2000

Related U.S. Application Data (60) Provisional application No. 60/188,307, filed on Mar. 10, 2000, provisional application No. 60/164,022, filed on Nov. 4, 1999, and provisional application No. 60/162,683, filed on Nov. 1, 1999.

(51) Int. Cl.[7] .............................................. G06F 13/00
(52) U.S. Cl. ........................ 702/22; 702/116; 702/120; 702/123
(58) Field of Search .......................... 702/22, 116, 120, 702/123; 600/345; 379/88.22

(56) References Cited

U.S. PATENT DOCUMENTS

| | | | |
|---|---|---|---|
| 5,528,363 A | | 6/1996 | Fachinger et al. ........... 356/326 |
| 5,554,539 A | * | 9/1996 | Chadney et al. ................ 436/8 |
| 5,571,401 A | | 11/1996 | Lewis et al. ................ 205/787 |
| 5,675,070 A | | 10/1997 | Gelperin ..................... 73/23.34 |
| 5,697,326 A | | 12/1997 | Mottram et al. ............. 119/174 |
| 5,788,833 A | | 8/1998 | Lewis et al. ................ 205/787 |
| 5,790,977 A | | 8/1998 | Ezekiel ........................ 702/122 |
| 5,807,701 A | | 9/1998 | Payne et al. ................... 435/34 |
| 5,891,398 A | | 4/1999 | Lewis et al. ............. 422/82.02 |
| 6,085,576 A | | 7/2000 | Sunshine et al. ........... 73/29.01 |
| 6,134,504 A | * | 10/2000 | Douglas et al. ................ 702/31 |
| 6,175,752 B1 | * | 1/2001 | Say et al. ..................... 600/345 |
| 6,234,006 B1 | | 5/2001 | Sunshine et al. ........... 73/29.01 |
| 6,263,458 B1 | * | 7/2001 | Miller et al. ................... 714/47 |
| 6,329,139 B1 | * | 11/2001 | Nova et al. ...................... 435/6 |
| 6,418,783 B2 | | 7/2002 | Sunshine et al. ........... 73/29.01 |
| 6,422,061 B1 | | 7/2002 | Sunshine et al. ........... 73/29.01 |
| 6,450,008 B1 | | 9/2002 | Sunshine et al. .......... 73/23.34 |
| 2002/0149466 A1 | | 10/2002 | Sunshine et al. ............. 338/34 |
| 2002/0152037 A1 | | 10/2002 | Sunshine et al. ............. 702/23 |

FOREIGN PATENT DOCUMENTS

| | | |
|---|---|---|
| EP | 0 789 239 A1 | 8/1997 |
| EP | 0 943 992 A2 | 9/1999 |
| GB | 2342171 A | 4/2000 |
| WO | WO 99/14882 | 3/1999 |
| WO | WO 99/47905 | 9/1999 |
| WO | WO 01/69186 A1 | 9/2001 |

\* cited by examiner

*Primary Examiner*—Marc S. Hoff
*Assistant Examiner*—Felix Suarez
(74) *Attorney, Agent, or Firm*—Townsend and Townsend and Crew, LLP; Horace H. Ng (57) ABSTRACT

The present invention relates to a computer program product or code in memory for detecting and transmitting sensory data from a portable field device 10 to a processor 12 via a computer network 10 for analytic purposes. The product includes a code directed to capturing analyte data pertaining to an unknown analyte using a field device 10. The product further includes a code directed to encoding the captured analyte data and transmitting the encoded analyte data via a computer network 18 to a processor 12 for analysis. The product also includes a code directed to performing an analysis of the captured analyte data at a remote location by the processor 12 using data of known analytes retrieved from an electronic library 14. This code and others can be used with the present invention to perform the functionality described herein as well as others.

33 Claims, 8 Drawing Sheets

COMPUTER CODE FOR PORTABLE SENSING

CROSS-REFERENCES TO RELATED APPLICATIONS

This application claims the benefit of priority from U.S. Provisional Patent Application Serial No. 60/164,022, filed on Nov. 4, 1999, U.S. Provisional Patent Application Serial No. 60/162,683, filed on Nov. 1, 1999, and U.S. Provisional Patent Application Serial No. 60/188,307, filed on Mar. 10, 2000, all of which are hereby incorporated by reference as if set forth in full in this document.

FIELD OF THE INVENTION

This invention generally relates to the detection and transmission of sensory data. More particularly, the present invention relates to computer code(s) for detecting and transmitting sensory data from one portable device to another for analytic purposes.

BACKGROUND OF THE INVENTION

Techniques and devices for detecting a wide variety of analytes in fluids such as vapors, gases and liquids are well known. Such devices generally comprise an array of sensors that in the presence of an analyte produce a unique output signature. Using pattern recognition algorithms, the output signature, such as an electrical response, can be correlated and compared to the known output signature of a particular analyte or mixture of substances. By comparing the unknown signature with the stored or known signatures, the analyte can be detected, identified and quantified. Examples of such detection devices can be found in U.S. Pat. No. 5,571,401(by Lewis et al. and assigned to California Institute of Technology); U.S. Pat. No. 5,675,070 (by Gelperin and assigned to NCR Corporation); U.S. Pat. No. 5,697,326 (by Mottram et al. and assigned to British Technology Group Limited); U.S. Pat. No. 5,788,833 (by Lewis et al. and assigned to California Institute of Technology); U.S. Pat. No. 5,807,701 (by Payne et al. and assigned to Aromascan PLC); and U.S. Pat. No. 5,891,398 (by Lewis et al. and assigned to California Institute of Technology), the disclosures of which are incorporated herein by reference.

Concurrent with the development of better detection techniques for detecting analytes, there is an emerging need to develop methods and devices to efficiently transmit the collected sensory data for swift analysis. Under some prior customary practices, the sensory data were first captured and then physically transported back to a laboratory or some other designated facility for subsequent analysis. Very often, analyses on these data would not be performed until a substantial period of time had elapsed and consequently their results would not be available for hours, days or even weeks.

Timely transmission and analysis of sensory data for detected analytes have tremendous applications in a variety of areas. There are many instances where it is desirable to obtain results on the analysis of the sensory data in a timely manner. For example, in a hospital/medical environment, it would be greatly beneficial if data collected from a patient can be transmitted quickly to a laboratory to determine the cause of the patient's ailments thereby allowing the doctors to prescribe the necessary treatment without any undue delay. In a similar example, medical and other related data from home monitoring devices can be collected and transmitted swiftly to the appropriate hospitals and/or authorities to allow them to provide better response to home emergencies. In another example, in environments where the presence of certain substances can potentially lead to dangerous conditions, such as a gas leak in a foundry or a home, the swift transmission of sensory data for analysis can very well preempt an impending disaster. Clearly, there are many other situations which one could think of where the efficient transmission of sensory data will generate tremendous benefits. Hence, it would be desirable and beneficial to provide a system that is capable of timely transmitting sensory data for analysis.

In addition to the need to have timely transmission of sensory data, there is a need to provide easy access to the collective data compiled for the known analytes. The results of any detection analysis are only as good as the data which are available for comparison. At the present time, various analytes have been identified and data therefor have been compiled and stored all over the world. Perhaps, due to the voluminous amount of data that are available, these data are generally not centralized in any one particular repository but are instead separately stored at different facilities. The segregation of these data, therefore, renders a complete and accurate analysis more difficult. Hence, it would be desirable to have a system that is capable of providing better access to various data repositories thereby allowing more accurate analyses to be performed. The present invention remedies these shortcomings by providing a system of transmitting, storing and retrieving sensory information.

SUMMARY OF THE INVENTION

The present invention generally relates to detecting and transmitting analyte data from a field device to a processor. In an exemplary embodiment, the present invention provides computer codes for capturing and transmitting analyte data over a computer network such as an internet, the Internet, a local area network, a wide area network or any combination thereof.

In a specific embodiment, the present invention provides a system including computer code for capturing and transmitting analyte data pertaining to an unknown analyte. The computer code is embedded in memory, which can be at a single location or multiple locations in a distributed manner. The system has a first code directed to capturing data for the unknown analyte using a field device at a first geographic location. The system also includes a second code directed to transmitting the captured analyte data to a processor at a second geographic location via a computer network. In a preferred embodiment, the captured analyte data are transferred via a worldwide network of computers such as an internet, the Internet, a combination thereof, and the like.

In one aspect, before the captured analyte data are transmitted, the system includes computer code directed to encoding the captured analyte data by the field device into a transmissible format. The system also includes computer code directed to decoding the encoded analyte data by the processor to permit analysis to be performed. In order to analyze the captured analyte data, the system further includes computer code directed to retrieving data of known analytes from an electronic library and performing the analysis using such data. In addition, the system includes computer code directed to updating the electronic library with the captured analyte data. This code and others can be used with the present invention to perform the functionality described herein as well as others.

By transmitting the captured analyte data via a computer network, the present invention provides a system including computer codes that is capable of transmitting analyte data in a timely and efficient manner. Consequently, analyses can be performed swiftly and results can be obtained on a more expedited basis.

Numerous benefits are achieved by way of the present invention over conventional techniques. For example, the present invention allows for the efficient transfer of analyte data from one geographic location to another geographic location thereby providing utility and applications in various areas such as hospital/medical applications, fire safety monitoring, environmental toxicology, remediation, biomedicine, material quality control, food monitoring, agricultural monitoring, heavy industrial manufacturing, ambient air monitoring, worker protection, emissions control, product quality testing, oil/gas petrochemical applications, combustible gas detection, $H_2S$ monitoring, hazardous leak detection, emergency response and law enforcement applications, explosives detection, utility and power applications, food/beverage/agriculture applications, freshness detection, fruit ripening control, fermentation process monitoring and control, flavor composition and identification, product quality and identification, refrigerant and fumigant detection, cosmetic/perfume applications, fragrance formulation, chemical/plastics/pharmaceuticals applications, fugitive emission identification, solvent recovery effectiveness, anesthesia and sterilization gas detection, infectious disease detection, breath analysis and body fluids analysis. Additionally, the present invention uses conventional computer hardware and/or software, which make it easy to implement.

Using a distributed computer network for collecting analyte data and then performing the analysis and interpretation remotely has a number of advantages. For example, every new piece of data can be added to the electronic library thereby continually expanding the repository of knowledge. This approach allows historical data to be kept and retrieved for subsequent use. In addition, with the use of an electronic library, data can be easily shared at different physical locations thereby facilitating objective data comparison. For instance, data relating to a product can be captured at various shipment checkpoints to provide quality control on the product. Finally, by providing the capability to have a number of field devices transmit data to a central location, a large area can be monitored for safety or other purposes.

Reference to the remaining portions of the specification, including the drawings and claims, will realize other features and advantages of the present invention. Further features and advantages of the present invention, as well as the structure and operation of various embodiments of the present invention, are described in detail below with respect to accompanying drawings. In the drawings, like reference numbers indicate identical or functionally similar elements.

DETAILED DESCRIPTION OF THE INVENTION AND SPECIFIC EMBODIMENTS

Figure 1:
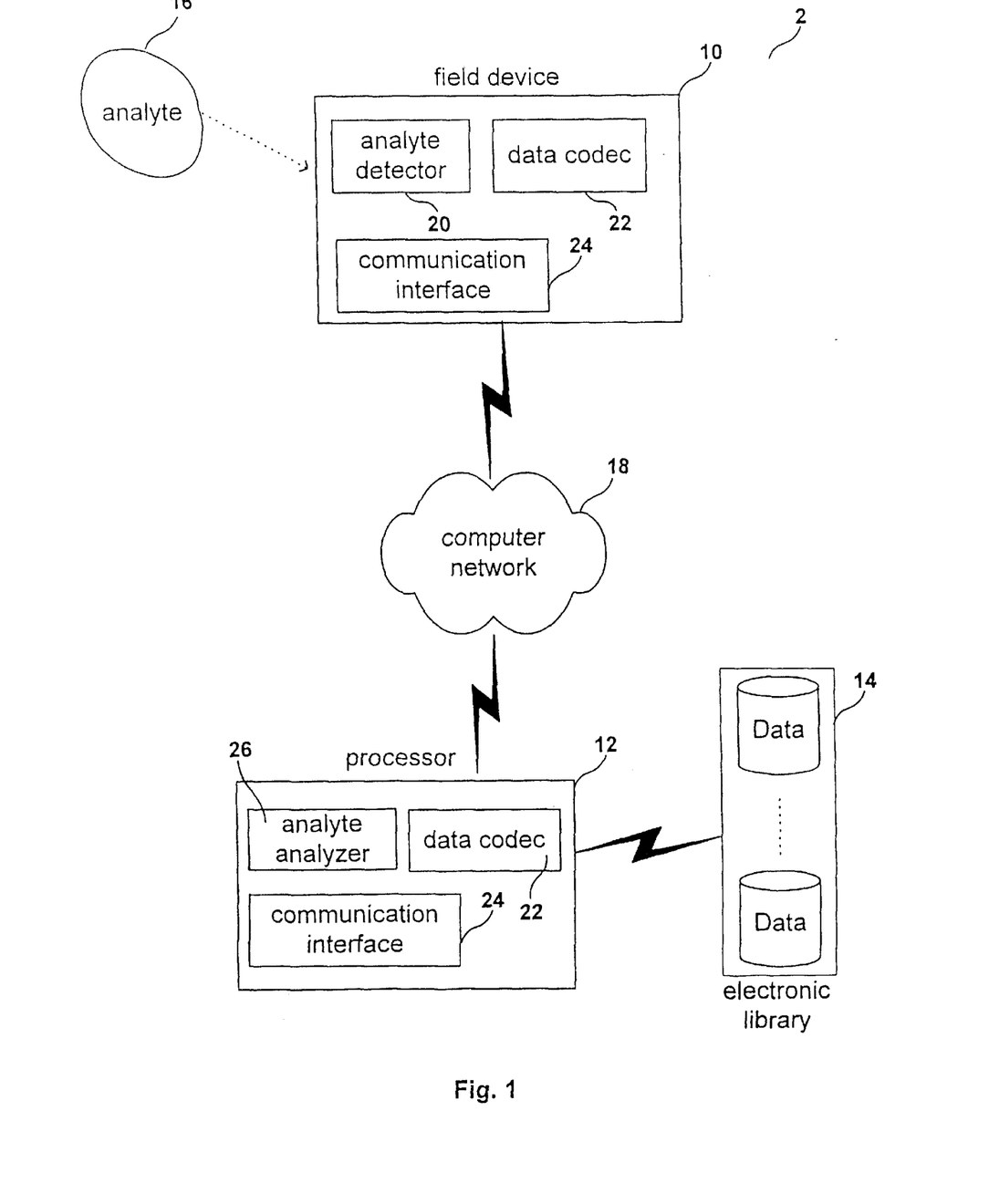
FIG. 1 is a simplified schematic block diagram showing a system according to one embodiment of the present invention.

FIG. 1 is a simplified schematic block diagram showing a detection and transmission system 2 according to an exemplary embodiment of the present invention. This diagram is merely an example which should not limit the scope of the claims herein. One of ordinary skill in the art would recognize many other variations, modifications, and alternatives. As shown, the system 2 preferably includes a field device 10, a processor 12 and an electronic library 14.

The field device 10 is capable of detecting an analyte 16 and transmitting the data relating to such analyte via a computer network 18 to the processor 12 for analysis. It should be understood that the field device 10 is generally capable of communicating with other devices connected to the computer network 18. In one embodiment, the field device 10 includes an analyte detector 20 and a data coder/decoder (codec) 22.

The analyte detector 20 is a transducer, such as an electronic nose, capable of detecting the presence of an analyte 16 and then generating certain sensory data corresponding to a unique output signature specific to the detected analyte. The analyte detector 20 may utilize one of many different detection techniques, such as electronic nose technology, gas chromatography, and mass spectrometry etc., to detect the presence of an analyte depending on the attendant circumstances. An illustrative implementation of the analyte detector is disclosed in U.S. patent application Ser. No. 271,873, which is now U.S. Pat. No. 6,085,576, commonly assigned, and hereby incorporated by reference for all purposes.

The main function of the data codec 22 is to encode and decode data exchanged between the field device 10 and the outside world. For example, the data codec 22 receives data from the analyte detector 20 and, after appropriate encoding or formatting, relays them to the processor 12 via the computer network 18. In other instances, data coming from the processor 12 are decoded by the data codec 22 to allow the data to be used by the field device 10. The data encoding or formatting steps will be described in further details below.

The data communications between the field device 10 and the outside world, such as the processor 12, can be either one-way or two-way communication. The field device 10 can act solely as a transmitter capable of only sending data to the processor 12, or alternatively, the field device 10 can act as a transceiver capable of both sending and receiving data from the processor 12.

The analyte detector 20 and the data codec 22 are preferably located within the same housing. The field device 10 can be a portable, handheld device such as the Palm® devices manufactured by 3Com and the Visor® produced by Handspring. By incorporating the analyte detector 20 and the data codec 22 in a portable, handheld device, a user has the additional ability to operate in a mobile manner. This mobility is obviously greatly desirable as the need to detect the presence of analytes often arises in limiting environments where cable, phone or other pre-installed communication outlets are not readily available or accessible. In one embodiment, the analyte detector 20 is described in U.S. patent application Ser. No. 271,873, which is now U.S. Pat. No. 6,085,576, commonly assigned, and hereby incorporated by reference for all purposes. As described therein, the analyte detector 20 is integrated into a hand-held device thereby permitting a user to conduct the analyte detection in a mobile manner.

In an alternative embodiment (not shown), the data codec 22 can be located on a gateway, such as a computer, connected to the computer network 18. Under this configuration, the field device 10 sends the captured analyte data to the gateway and the data codec 22 processes the data and forwards them to the processor 12 via the computer network 18.

The processor 12 includes a data codec 22 and an analyte analyzer 26. Similar to the data codec 22 in the field device 10, the function of the data codec 22 in the processor 12 is to encode and decode data exchanged between the processor 12 and the outside world. For example, the data codec 22 receives data from the field device 10 via the computer network 18 and processes or decodes the data into a format which can be understood by the analyte analyzer 26; similarly, the data codec 22 can also format or encode data so as to allow the processor 12 to transmit them to the field device 10. In other instances, the data codec 22 also encodes or decodes the data so as to allow such data to be exchanged between the processor 12 and the electronic database 14.

The analyte analyzer 26 is capable of performing analysis on a detected analyte. Using data stored in the electronic library 14 and after appropriate formatting by the data codec 22, the analyte analyzer 26 compares data received from the field device 10 with data retrieved from the electronic database 14 to identify the identity of the detected analyte. The results of the analysis can then be formatted by the data codec 22 for posting onto the electronic library 14. In addition, the results can be made available to the field device 10 in a number of ways. For example, the processor 12 can directly send the results back to the field device 10 via the computer network 18, or, the results can be formatted in HTML and displayed on a web page which can then be accessed by the field device 10 to retrieve the results.

The analyte analyzer 26 uses a number of pattern recognition algorithms to compare the output signature of the detected unknown analyte to the signatures of known analytes. Many of the algorithms are neural network based algorithms. A neural network has an input layer, processing layers and an output layer. The information in a neural network is distributed throughout the processing layers. The processing layers are made up of nodes that simulate the neurons by its interconnection to their nodes.

In operation, when a neural network is combined with a sensor array, the sensor data is propagated through the networks. In this way, a series of vector matrix multiplications are performed and unknown analytes can be readily identified and determined. The neural network is trained by correcting the false or undesired outputs from a given input. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In a preferred embodiment, the Fisher linear discriminant analysis (FLDA) and canonical discriminant analysis (CDA) and combinations thereof are used to compare the output signature and the available data from the electronic library. The operating principles of various algorithms suitable for use in the present invention are disclosed (see, Shaffer et al., *Analytica Chimica Acta*, 384, 305–317 (1999)), the teaching of which are incorporated herein by reference.

In order to determine which pattern recognition algorithm is optimal for the analysis of a particular detected analyte, the processor 12 is trained using various sets of training data. The subject of training devices for classification or identification purposes for one or more substances capable of producing sensory information is covered by a series of patent applications, U.S. Patent Application Serial No. 60/188,589, filed on Mar. 10, 2000, U.S. Patent Application Serial No. 60/188,588, filed on Mar. 10, 2000, and U.S. Patent Application Serial No. 60/188,569, filed on Mar. 10, 2000, all commonly owned, and hereby incorporated by reference for all purposes.

With respect to the electronic library 14, it generally contains signatures for various known analytes and other relevant information pertaining to these analytes. The electronic library 14 can be composed of a number of different databases. These databases can be located in one central repository, or alternatively, they can be dispersed among various distinct physical locations. These databases can be categorized and structured in various ways based on the needs and criteria of the database designer. For example, the data can be organized in a database using field descriptors. Field descriptors can include the sample name, type of data etc. Possible types of data include training data, identification data, or quality control data. As another example, a first database may contain data relating to various types of analytes collected using the same detection technique under a standardized set of conditions, and a second related database may contain miscellaneous information correlating to data contained in the first database; more specifically, a first database may contain aroma data for various types of wines, and a second database may contain additional information for each type of wine identified in the first database such as the vineyard, type of wine, year of bottling, etc. Alternatively, a database may contain data specific to one particular analyte with such data collected using different detection techniques. Methods used to create and organize databases are commonly known in the art, for example, relational database techniques can be used to logically connect these databases.

In one embodiment, as shown in FIG. 1, the databases comprising the electronic library 14, or a portion thereof, can be physically located separate from the processor 12. These databases can reside on remote, distant servers on a local area network or the Internet. Under this arrangement, whenever any data are needed, the processor 12 needs to access the necessary database(s) via a communication channel to retrieve the requisite data for analysis. For example, the processor 12 can access and retrieve data from a remote database via a computer network such as a LAN or the Internet.

Figure 6:
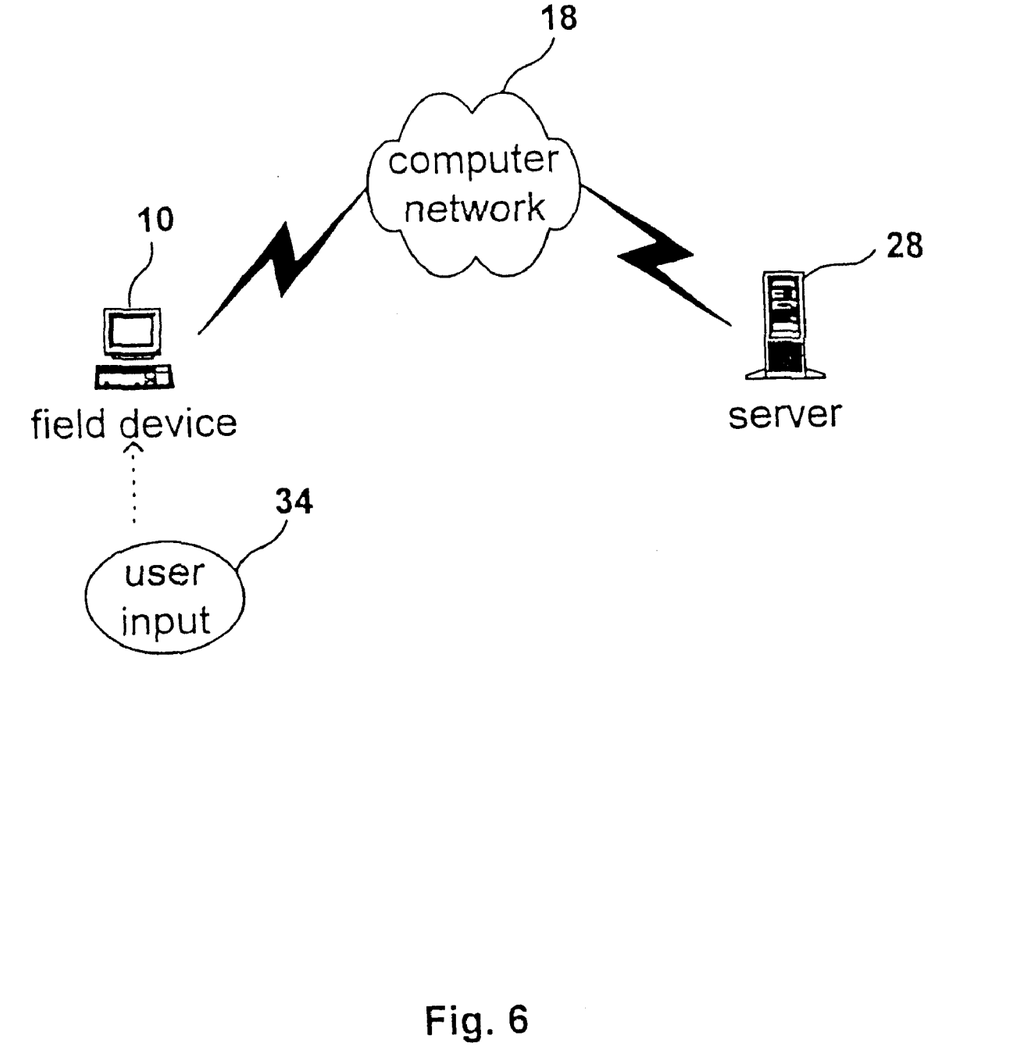
FIG. 6 is a simplified schematic block diagram showing a system according to a fourth embodiment of the present invention.

FIG. 6 illustrates another embodiment of the present invention. This diagram is merely an example which should not limit the scope of the claims herein. One of ordinary skill in the art would recognize many other variations, modifications, and alternatives. In this embodiment, the electronic library 14 is located on the same machine as the processor 12. For example, the processor 12 can reside on a server 28 hosting a website and the electronic library 14 can similarly reside on the same server 28. With this arrangement, the electronic library 14 and the data contained therein are readily accessible for use by the processor 12.

The data in the electronic library 14 can be stored in a number of different formats. For example, the data can be formatted into HTML documents which can then be made accessible on the Internet from any remote location.

Since data are constantly provided to the electronic library 14 during operation of the present invention, the electronic library 14 may need to be updated on a periodic basis to keep the size of the electronic library 14 manageable. Various schemes can be used to update the electronic library 14. In one scheme, the older data are discarded after some predetermined period of time. In another scheme, the older data are averaged and then compressed on a regular basis so as to make room for the more recently captured data. In yet another scheme, the more recent data are stored in the database only when such data represent an exception or deviation.

A number of different technologies can be used to implement the communications between the field device 10, the processor 12 and the electronic library 14. As to communications between the field device 10 and the processor 12, such communications can be conducted via a computer network 18. In order to provide a physical connection to the outside world for the transmission of captured analyte data, the field device 10 includes a communication interface 24 that is capable of being coupled to the computer network 18. The communication interface 24 may include an Ethernet interface, an RS-232 interface, a parallel port, a universal serial bus (USB), an infrared data link, an optical interface, or an RF interface. The computer network 18 can be one of a variety of networks including a worldwide computer network, an internet, the Internet, a WAN, a LAN or an intranet. It should be understood that conventional access to the computer network is conducted through a gateway (not shown). A gateway is a machine, for example, a computer, that has a communication address recognizable by the computer network.

The field device 10 can communicate with the computer network 18 via the communication interface 24 using either wireless or wired technologies. Wireless technologies may include infrared, radio waves, satellite and microwaves. Wired technologies may include cables and modems.

Figure 2:
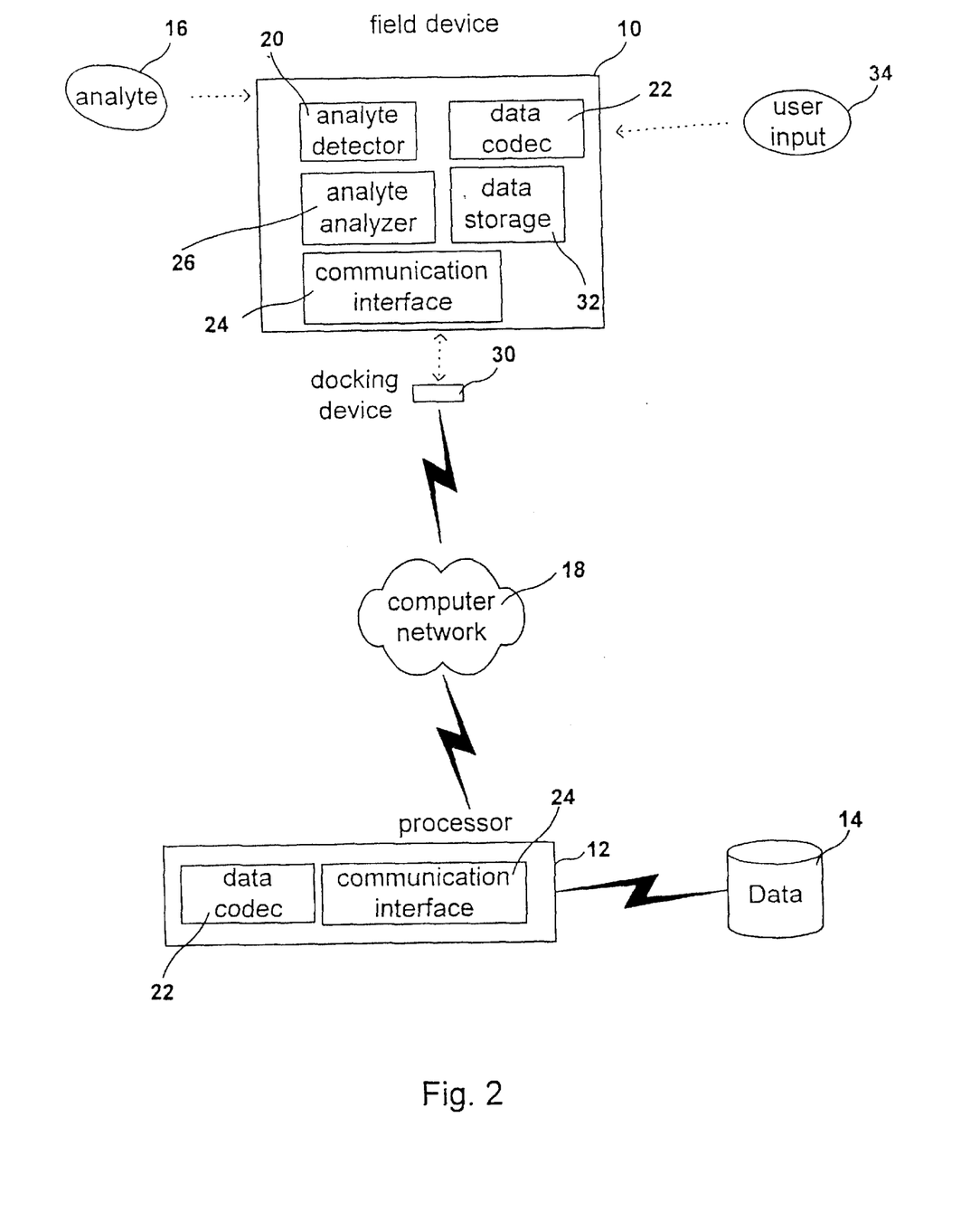
FIG. 2 is a simplified schematic block diagram showing a system according to a second embodiment of the present invention.

FIG. 2 illustrates another embodiment of the present invention. This diagram is merely an example which should not limit the scope of the claims herein. One of ordinary skill in the art would recognize many other variations, modifications, and alternatives. As shown therein, the field device 10 can be detachably coupled to a docking device 30 which, in turn, is connected to a gateway on the computer network 18.

Figure 3:
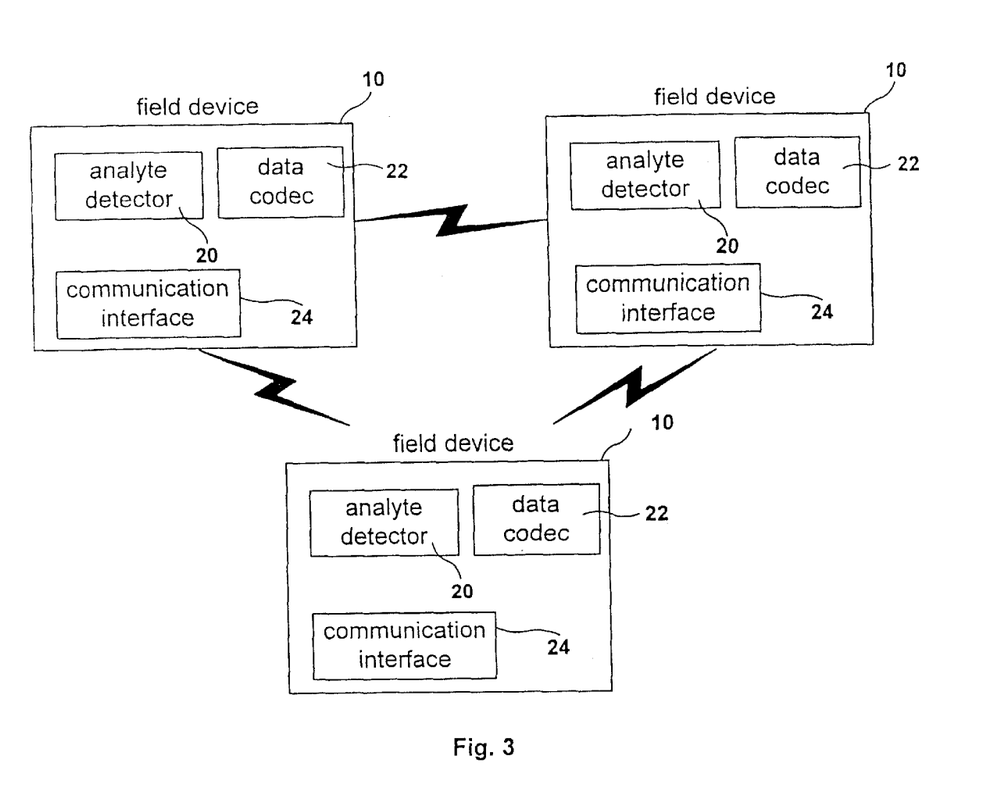
FIG. 3 is a simplified schematic block diagram showing a system according to a third embodiment of the present invention.

FIG. 3 illustrates yet another embodiment of the present invention. This diagram is merely an example which should not limit the scope of the claims herein. One of ordinary skill in the art would recognize many other variations, modifications, and alternatives. As shown therein, field devices 10 may be able to communicate with one another directly. In this device-to-device type of communication, infrared signals are generally used.

As to communications between the processor 12 and the electronic library 14, such communications can also be conducted via a computer network 18 or other communication links such as a modem. Similarly, the processor 12 also includes a communication interface 24 to allow the processor 12 to communicate with other devices. Also, as mentioned above, depending on various requirements, the electronic library 14 can reside on the same machine as the processor 12, thereby reducing communication overhead and costs.

The field device 10 generally performs the following steps before the captured analyte data are delivered to the computer network 18 for transmission: (1) capturing analyte data in analog form; (2) converting the analog data into digital data; (3) encoding digital data into an analysis format; (4) encoding data in analysis format into a TCP/IP format; and (5) encoding data in TCP/IP format into a specific network data format.

At the receiving end, the processor 12 generally performs the following steps to decode the encoded data: (1) receiving data in specific network data format; (2) decoding the received data into TCP/IP format; and (3) decoding the data in TCP/IP format into an analysis format.

Figure 4:
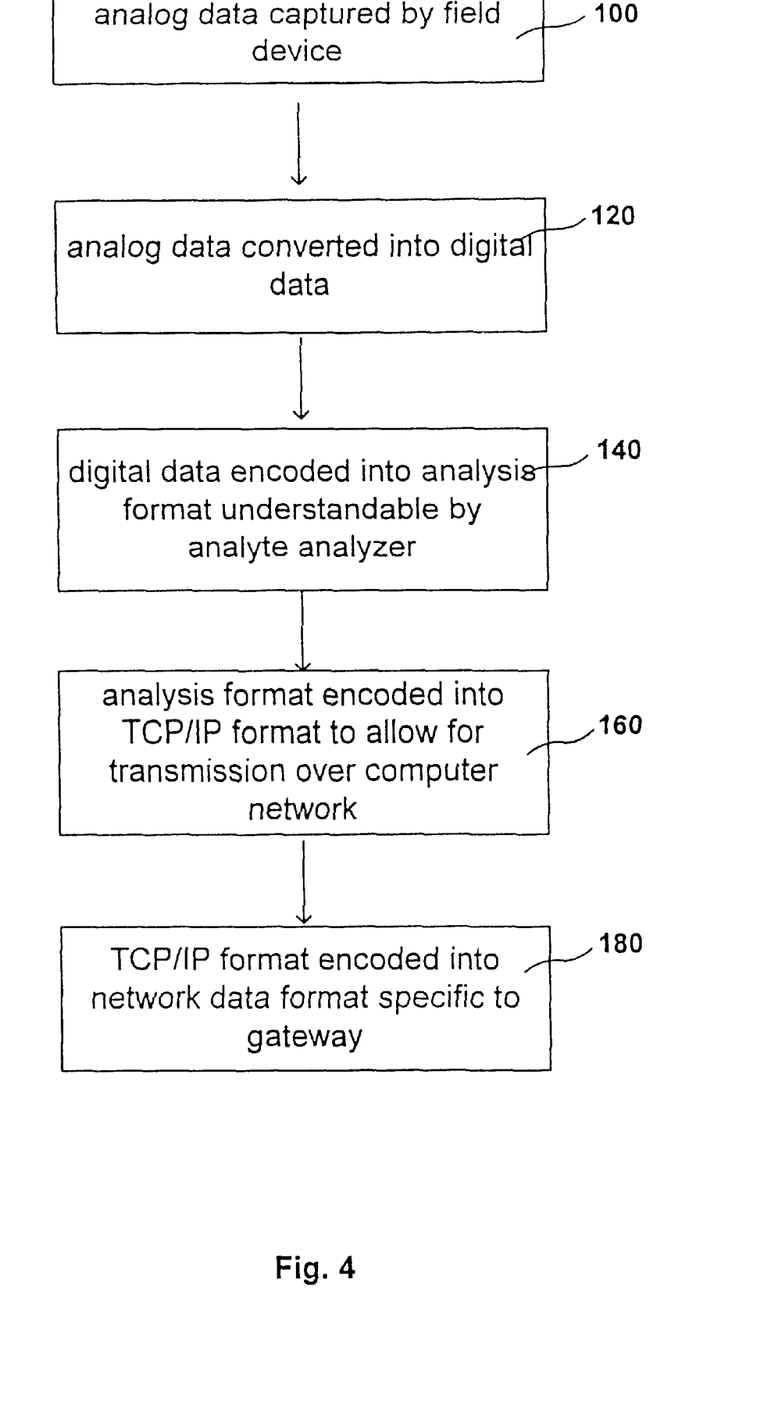
FIG. 4 is a simplified flow diagram showing the process of encoding the data in accordance with the present invention.

Details of these steps will now be described with reference to FIGS. 4 and 5. FIG. 4 illustrates the various data encoding formats needed to convert the analog data from the detected analyte into a transmissible format for transmission to the processor 12. This diagram is merely an example which should not limit the scope of the claims herein. One of ordinary skill in the art would recognize many other variations, modifications, and alternatives. At step 100, analog data from the detected analyte are first captured by the analyte detector 20 in the field device 10. The analyte detector 20 acting as a transducer then converts the analog data into digital signals at step 120. At step 140, the digital signals are encoded into an analysis format which can be understood by the analyte analyzer 26. This format can be either proprietary or well-known. Any format can be used as long as the analyte analyzer 26 is capable of handling such format. While it is not necessary that the format used by the field device 10, the processor 12, and the electronic library 14 must be the same, a standardized format is preferred since format-conversion overhead can be saved. At step 160, the formatted data are further encoded into a format which can be transmitted over the computer network 18, such as the TCP/IP format. This step 160 is important if the formatted data are to be sent to the processor 12 via a computer network 18, such as the Internet, which contains numerous sub-networks having different network data formats. At step 180, the data in TCP/IP format are encoded into the specific network data format which the gateway to the computer network 18 can understand.

Figure 5:
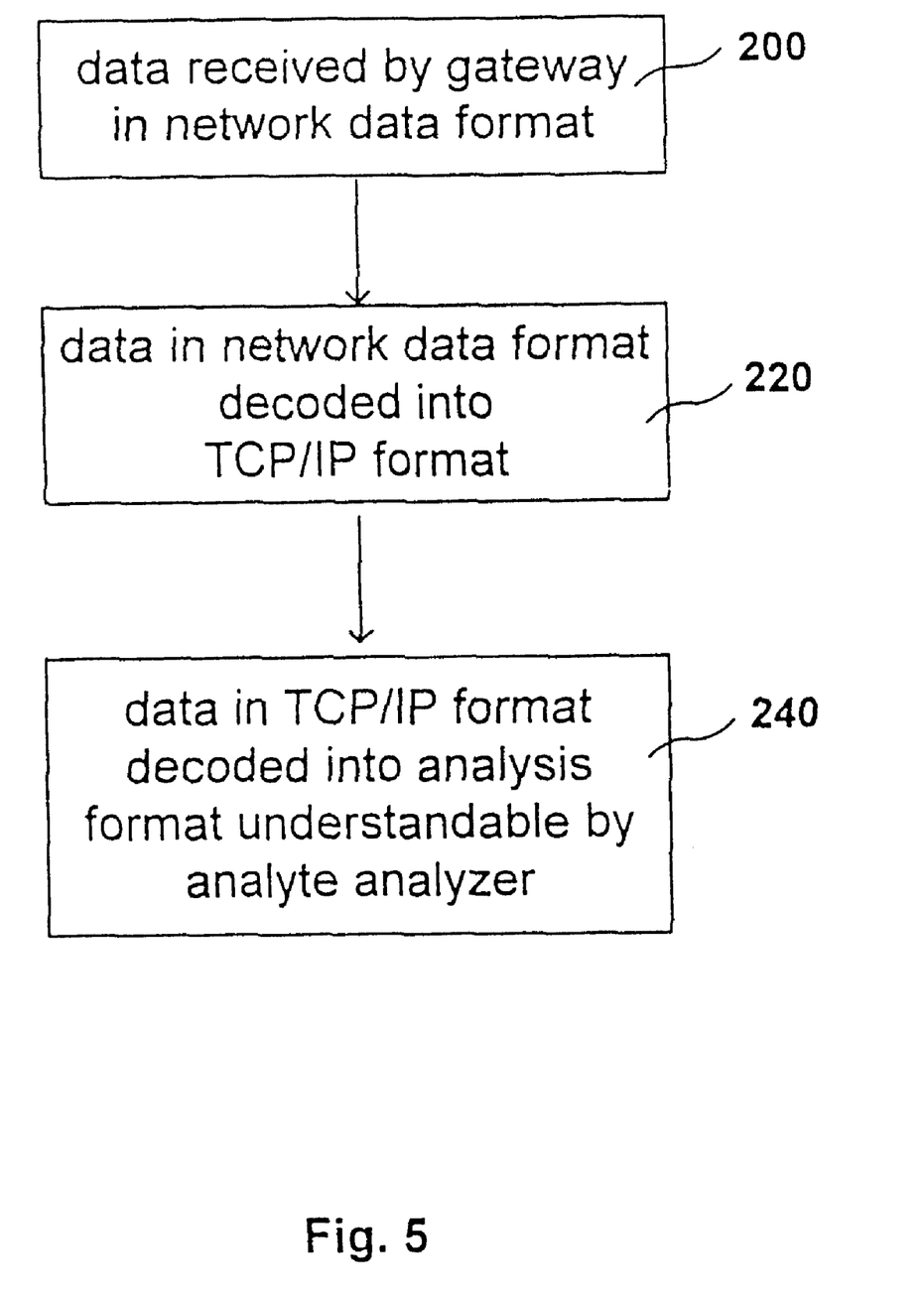
FIG. 5 is a simplified flow diagram showing the process of decoding the data in accordance with the present invention.

FIG. 5 illustrates the various data decoding formats needed to convert the transmitted data received from the field device 10 to permit analysis by the processor 12. This diagram is merely an example which should not limit the scope of the claims herein. One of ordinary skill in the art would recognize many other variations, modifications, and alternatives. At step 200, data transmitted from the field device 10 via the computer network 18 are received by the gateway in a network data format specific to the gateway. At step 220, the data in the network data format are decoded into the TCP/IP format. At step 240, the data in TCP/IP format are further decoded into an analysis format which can be used by the analyte analyzer 26 for analysis.

The present invention can be used in a number of different ways. In one mode of operation, a user first uses the field device 10 to capture information on an unknown analyte 16, and then relays the captured information to the processor 12 for analysis. More specifically, the analyte detector 20 is used to detect the presence of an unknown analyte 16. The analyte detector 20 then accordingly generates a unique output signature for this unknown analyte 16. The unique output signature is next relayed to the data codec 22 and encoded for transmission to the processor 12.

The data codec 22 in the processor 12 accepts the output signature from the field device 10 and then, after appropriate processing, passes it onto the analyte analyzer 26 for analysis. Depending on the detection technique used to detect the unknown analyte 16 and other relevant information which can be provided by the user, the processor 12 accesses the electronic library 14 retrieving the pertinent data corresponding to the signatures of various known analytes. The analyte analyzer 26 then compares the output signature with these known signatures to ascertain the identity of the detected analyte. If desired, the results of the comparison are transmitted to the field device 10 from the processor 12 for use by the user. Alternatively, the results of the comparison can be posted onto a web page for retrieval by the field device 10.

Optionally, if the output signature of the detected analyte is determined to be not currently included in the electronic library 14, the processor 12 can then appropriately update the electronic library 14 to reflect the new output signature and its accompanying information.

For example, the present invention can be used to detect chemical leaks. Data relating to the harmful chemical are captured by the field device 10 and relayed to the processor 12. The processor 12 compares the captured data to data available from the electronic library 14 to ascertain the identity of the chemical. Results of the comparison are then sent to the field device 10 to enable the user to initiate the necessary remedial measures, if any, to limit further damage. Optionally, in the event that the identity of the chemical cannot be determined using the data currently existing in the electronic library 14, the processor 12 will update the electronic library 14 to reflect the discovery of this "new" chemical for future identification.

In another mode of operation, field devices 10 are capable of communicating and exchanging data with one another using their respective communication interfaces 24. The primary purpose here is to allow sharing of data between the two devices 10. In the event that multiple field devices 10 (employing the same detection technique) are used to detect the same unknown analyte, data collected from these devices 10 can be used by the processor 12 for calibration purposes to provide for any use-to-use variability of a field device 10.

In another embodiment, as shown in FIG. 6, the field device 10 can be a remote computer capable of connecting to the Internet, the processor 12 can be an interactive website residing on a remote server 28 connected to the Internet, and the electronic library 14 can be located on the same remote server 28. In a mode of operation in accordance with this embodiment, the user uses the field device 10 to retrieve information for certain analytes which are similar or related to a known, desired analyte. More specifically, the user enters the relevant information for the desired analyte into the field device 10. The field device 10, via the communication interface 24, transmits the entered information to the processor 12. The processor 12 processes the entered information and retrieves from the electronic library 14 the corresponding signature for the desired analyte.

Having retrieved the corresponding signature, the processor 12 then searches the electronic library 14 to identify a group of analytes which are similar or related to the analyte desired by the user by comparing the corresponding signature with other known signatures.

Additional information concerning each analyte within this identified group can be retrieved from other databases, if necessary. The identity of each analyte within the identified group and all the accompanying information are subsequently transmitted to the field device 10 for use by the user. Optionally, other information entered by the user can be used to narrow the identified group of analytes.

For example, the present invention can be used in a wine store to help consumers identify a wine list based on their personal tastes and preferences. In addition to different tastes, most wines also have their own distinctive aromas. Therefore, an electronic library storing data on wine aromas and other relevant information can be created. If a consumer has previously enjoyed a particular wine and can provide sufficient information about that wine, the present invention can be used to compile a list of comparable wines which the consumer may similarly enjoy. Using the present invention, this wine list can be further narrowed based on other factors such as country of origin, price, availability, shipping costs, and prior selections, etc.

Figure 7:
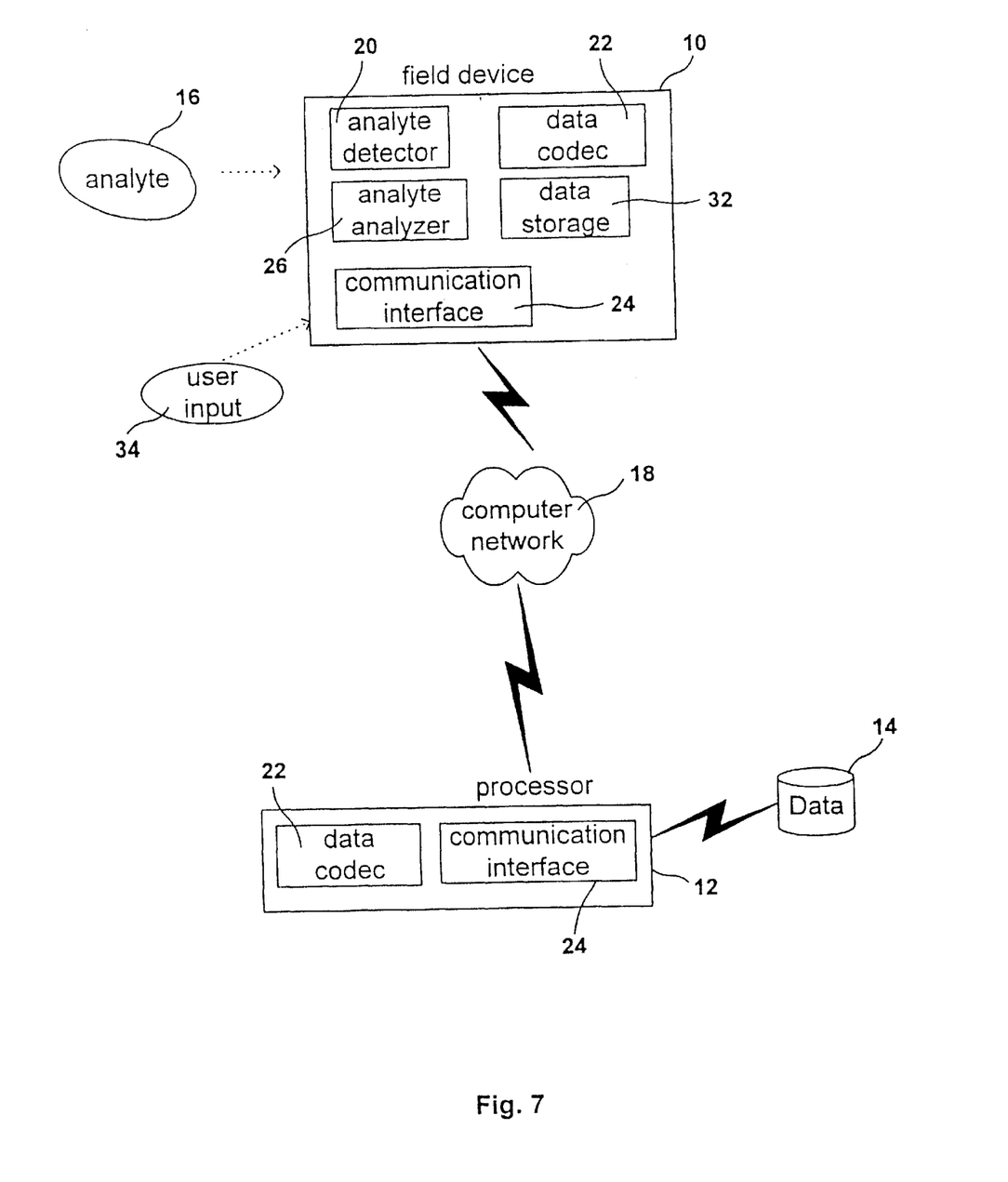
FIG. 7 is a simplified schematic block diagram showing a system according to a fifth embodiment of the present invention.

FIG. 7 illustrates an alternate embodiment of the present invention. This diagram is merely an example which should not limit the scope of the claims herein. One of ordinary skill in the art would recognize many other variations, modifications, and alternatives. As shown therein, certain components of the processor 12, such as the analyte analyzer 26, can reside within the field device 10. The analyte analyzer 26 is included within the field device 10 as opposed to the processor 12 and the field device 10 further includes a data storage area 32. With this particular configuration, the present invention may be operated in the following manner. The user enters a request 34 into the field device 10 for data relating to certain specified, known analytes. The field device 10 then transmits the request 34 to the processor 12. The processor 12, in turn, retrieves the relevant data from the electronic library 14 in accordance with the request 34 and forwards the requested data to the field device 10. Upon receipt of the requested data, the field device 10 stores them in a data storage area 32 for subsequent use. When the field device 10 is used to detect an unknown analyte 16, data in the data storage area 32 are readily available for use by the analyte analyzer 26 to compare and identify the detected analyte 16.

By having the analyte analyzer 26 and the data storage area 34 incorporated into the field device 10, the time required for analysis can be shortened. For example, prior to entering a particular area, if the user knows that there is a relatively high probability of presence of certain known analytes in that area, the user can download the signatures of these known analytes onto the field device 10 ahead of time. With the signatures readily available within the field device 10, the output signature of the detected analyte 16 can be compared against these known signatures first. Therefore, there may not be a need to connect to the processor 12 thereby allowing the analysis to be performed more quickly. Connection to the processor 12 only needs to be made when none of the downloaded signatures matches with that of the detected analyte 16.

The present invention can be used in many different applications. In certain embodiments, the system of the present invention can be used for monitoring medical conditions and disease processes. For instance, WO 98/29563, published Jul. 9, 1998, and incorporated herein by reference, discloses a method for monitoring conditions in a patient wherein a sample is obtained from a patient over a period of time. The samples are then flowed over a gas sensor and a response is measured. Thereafter, the response is correlated with known responses for known conditions. The conditions include, but are not limited to, the progression and/or regression of a disease state, bacterial infections, viral, fungal or parasitic infections, the effectiveness of a course of treatment and the progress of a healing process.

In certain instances, the patient is in a nursing home, primary residence or hospital. The patient uses the field device 10 to capture data on an analyte such as, but not limited to, a breath sample, which the patient provides. The data on the breath sample can be optionally transmitted over the Internet or intranet to the processor 12 and then be subsequently analyzed or read by a medical professional at a health company, doctors office or hospital. Using the system of the present invention, real time home health management is realized.

In certain aspects, the analyte data, such as olfaction data, vital signs and any other symptoms of the patient are transmitted to a second location. The data can then be analyzed and the medical condition and disease process monitored. Thereafter, the patient can access the diagnostic information on a private Web site for further instructions and treatment.

In other aspects, the system of the present invention can be used for monitoring chronic diseases which generally have associated with them distinctive odors or smells. For example, the system of the present invention can be used for monitoring medical conditions in a respiring subject. For instance, WO 98/39470, published Sep. 11, 1998, and incorporated herein by reference, discloses a method for detecting the occurrence of a condition in a respiring subject. The method comprises introducing emitted respiratory gases to a gas sensing device, detecting certain species present in the gas and correlating the presence of the species with certain conditions.

A wide variety of conditions can be ascertained using this aspect of the present invention. These conditions include, but are not limited to, halitosis, ketosis, yeast infections, gastrointestinal infections, diabetes, alcohol, phenylketonuria, pneumonia, and lung infections. Those of skill in the art will know of other conditions and diseases amenable to the method and system of the present invention.

In yet another embodiment, the system of the present invention can be used for monitoring conditions and disease processes in female patients. For instance, WO 99/09407, published Feb. 25, 1999, and incorporated herein by reference, discloses a method for detecting the occurrence of a condition in a female patient comprising obtaining a sample of gaseous or volatile substance from the vaginal region of the patient, detecting the gas and correlating the detection with the occurrence of a condition. A wide variety of conditions can be ascertained using this aspect of the present invention. These conditions include, but are not limited to, cervical cancer, ovarian or uterine cancer, HIV, sexually transmitted diseases, cytomegalovirus, yeast infections, pregnancy and Chlamydia.

In still yet another embodiment, the system of the present invention can be used for monitoring conditions and disease processes using a device that affixes to a portion of the skin on a subject. For instance, WO 99/09408, published Feb. 25, 1999, and incorporated herein by reference, discloses a method for detecting a condition of a subject with a device that is adapted to be affixed to the subject and having a gas sensing means disposed so as to detect gases and volatile species emanating from a portion of the skin. A wide variety of conditions can be ascertained using this aspect of the present invention. These conditions include, but are not limited to, skin cancer, diabetes, heart disease, heavy metal in the subject and drugs.

Figure 8:
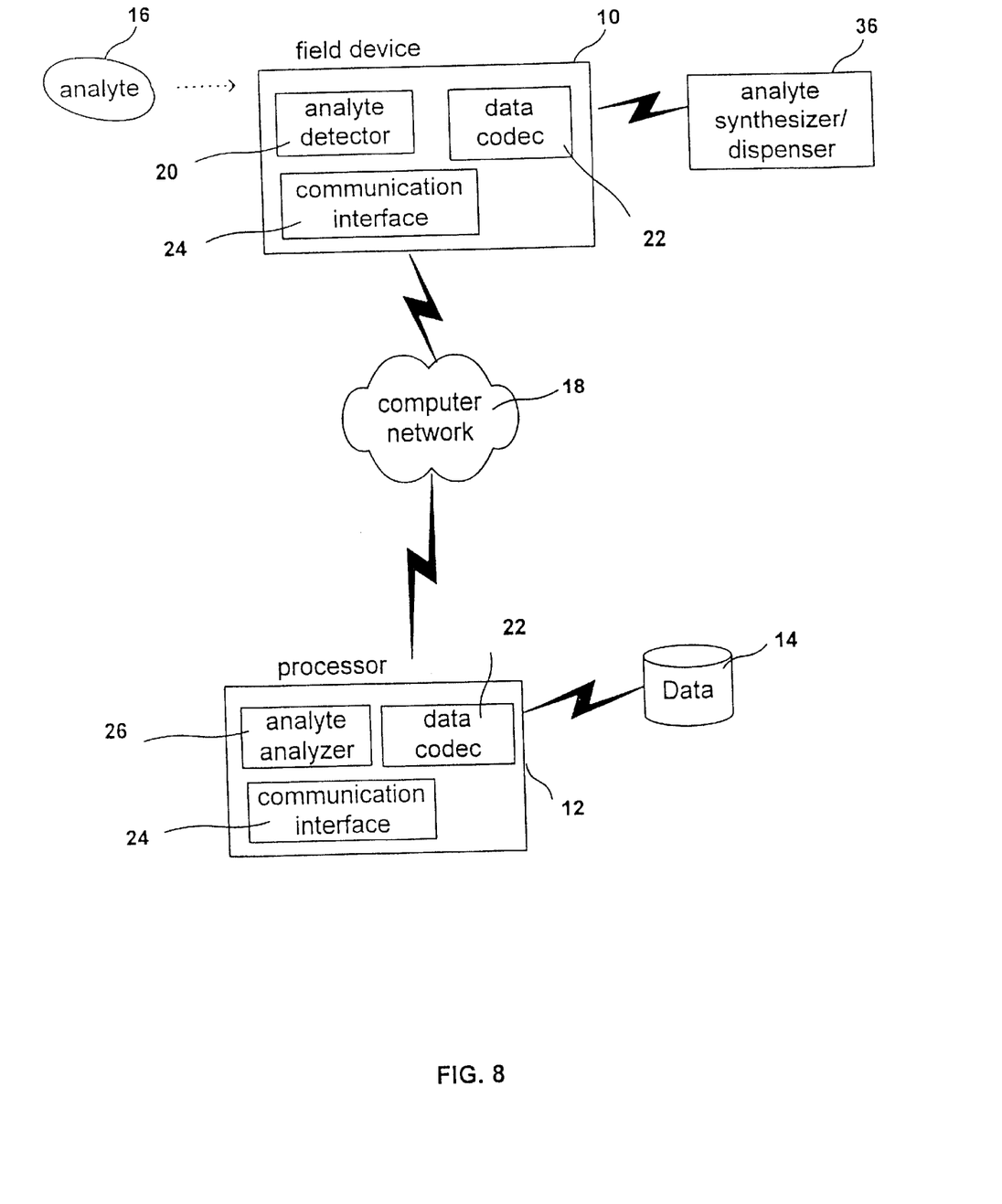
FIG. 8 is a simplified schematic block diagram showing a system according to a sixth embodiment of the present invention.

FIG. 8 illustrates yet another embodiment of the present embodiment. This diagram is merely an example which should not limit the scope of the claims herein. One of ordinary skill in the art would recognize many other variations, modifications, and alternatives. As shown therein, the present invention includes an analyte synthesizer or dispenser 36. The analyte synthesizer 36 is a device which is capable of synthesizing or dispensing analytes based on input information and parameters. The analyte synthesizer/dispenser 36 can be coupled to the field device 10 to receive the relevant analyte information. A conventional analyte synthesizer is the "iSmell™" synthesizer, or personal scent synthesizer available from Digiscents (Oakland California). The iSmell™ synthesizer is a software-controlled computer peripheral device that is capable of emitting a broad range of fragrances, smells and aromas using a combination and synthesis of primary odorants.

This embodiment may be used in the following manner. The signature of a known analyte is relayed by the field device 10 to the analyte synthesizer/dispenser 36 and thereafter the known analyte is reconstructed to produce either the actual fragrance, aroma, scent, or smell or a simulated version thereof. In addition, other analytes which are similar to the known analyte can also be reconstructed to offer a wider range of selection.

This embodiment including the analyte synthesizer/dispenser 36 can be used for various purposes. For example, an electronic library 14 can contain signatures of a myriad of consumer products including, but not limited to, perfumes, cigars, liquor, coffee, cosmetics, lipsticks, tobacco and wine. Using the system of the present invention, a consumer can, for example, physically smell a reconstructed sample of a particular brand of perfume having a characteristic signature, and if the consumer enjoys this brand of perfume, it is possible to suggest and then synthesize other perfumes with similar signatures that the consumer may also enjoy to provide a wider consumer choice.

The present invention can further be used for medical purposes, for example, delivering an odorant for inhalation via a computer network so as to stimulate the male sexual response. As described in U.S. Pat. No. 5,885,614, which issued to Hirsch, on Mar. 23, 1999, the use of odorants are useful for inducing or enhancing an erection, and as aids for a non-invasive treatment of male vasculogenic impotence. As described therein, the administration of odorants for inhalation by a male individual having a normal olfactory ability effectively increased penile blood flow from about 2–40%, and enhanced sexual arousal. Preferred odorants are those that provided a 20–40% increase in blood flow to the penis, which includes lavender, oriental spice, cola and orange, and odorant mixtures of lavender and pumpkin pie, doughnut and black licorice, and pumpkin pie and doughnut. The odorants are useful as adjuvants to augment penile blood flow and as aids in the treatment of male impotence, and to enhance sexual arousal in normal males, i.e., those without sexual dysfunction. The signature of the desired odorant is transmitted via the Internet to the analyte synthesizer/dispenser 36. The desired odorant is thereafter synthesized and/or dispensed to the male by inhalation.

It is understood that, based on the disclosure provided herein, the system of the present invention, or portions thereof, and the functionality described in connection therewith, can be implemented in many different ways by one of ordinary skill in the art. In an exemplary embodiment, the system of the present invention and its functionality are implemented using computer code and/or software programming techniques in a modular manner. However, many other ways of implementing the present invention are available as should be apparent to a person of ordinary skill in the art.

It is also understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes in their entirety.

What is claimed is:

1. A system comprising memory including a computer code product for detecting and transferring data pertaining to an analyte from a first device to a second device, said memory comprising:
    a code directed to capturing analyte data pertaining to said analyte using said first device;
    a code directed to transmitting said analyte data via a computer network to said second device;
    a code directed to encoding said analyte data into a transmissible format for transmission via said computer network to said second device;
    a code directed to decoding said analyte data in said transmissible format; and
    a code directed to directing said second device to perform an analysis on said analyte data.

2. A system according to claim 1, wherein said code directed to encoding further comprises:
    a code directed to capturing said analyte data in an analog format;
    a code directed to converting said analyte data in analog format into a digital format;
    a code directed to encoding said analyte data in digital format into an analysis format;
    a code directed to encoding said analyte data in analysis format into TCP/IP format; and
    a code directed to encoding said analyte data in TCP/IP format into a network-specific data format.

3. A system according to claim 1, wherein said code directed to decoding further comprises:
    a code directed to decoding said analyte data in a network-specific data format into TCP/IP format; and
    a code directed to decoding said analyte data in TCP/IP format into an analysis format.

4. A system according to claim 1, further comprising a code directed to retrieving signatures of known analytes from an electronic library.

5. A system according to 4, further comprising a code directed to analyzing said analyte data using said retrieved signatures.

6. A system according to claim 5, wherein said codes directed to retrieving and analyzing respectively are executed by said second device.

7. A system according to claim 4, wherein said electronic library includes one or more databases.

8. A system according to claim 5, further comprising a code directed to displaying result of execution of said code directed to analyzing on a web page.

9. A system according to claim 4, further comprising a code directed to updating said electronic library with said analyte data;
    wherein said code directed to updating is executed by said second device.

10. A system according to claim 1, wherein said transmission of said analyte data is conducted via wireless communications.

11. A system according to claim 10, wherein said wireless communications are implemented using communications technologies selected from a member of a group consisting of infrared technology, satellite technology, microwave technology and radio wave technology.

12. A system according to claim 1, wherein said transmission of said analyte data is conducted via wired communications.

13. A system according to claim 1, wherein said computer network is selected from a member of a group consisting of a worldwide computer network, an internet, the Internet, a wide area network, a local area network, and an intranet.

14. A system according to claim 1, wherein said first device is a handheld device.

15. A system according to claim 1, wherein said analyte data is olfaction data.

16. A system according to claim 1, wherein said system is used in an application selected from a group consisting of hospital/medical applications, fire safety monitoring, environmental toxicology, remediation, biomedicine, material quality control, food monitoring, agricultural monitoring, heavy industrial manufacturing, ambient air monitoring, worker protection, emissions control, product quality testing, oil/gas petrochemical applications, combustible gas detection, $H_2S$ monitoring, hazardous leak detection, emergency response and law enforcement applications, explosives detection, utility and power applications, food/beverage/agriculture applications, freshness detection, fruit ripening control, fermentation process monitoring and control, flavor composition and identification, product quality and identification, refrigerant and fumigant detection, cosmetic/perfume applications, fragrance formulation, chemical/plastics/pharmaceuticals applications, fugitive emission identification, solvent recovery effectiveness, anesthesia and sterilization gas detection, infectious disease detection, breath analysis and body fluids analysis.

17. A system including memory and computer codes for detecting and transferring analyte data, said system comprising:
    a code directed to capturing said analyte data using a first device or a second device;
    a code directed to converting said analyte data into a transmissible format;
    a code directed to transmitting said converted analyte data in said transmissible format from said first device or said second device; and
    a code directed to receiving said transmitted data in said transmissible format using said first device or said second device;
    wherein said first device and said second device are functionally equivalent.

18. A system according to claim 17, wherein said transmission of said converted analyte data is conducted via wireless communications.

19. A system according to claim 17, wherein said wireless communications are implemented using infrared technology.

20. A system including memory and computer codes for identifying an analyte, said system comprising:

a code for capturing at a first location data pertaining to said analyte whose identity is unknown;

a code for transmitting said data from said first location via a computer network;

a code for receiving said data at a second location; and a code for comparing said received data at said second location to data pertaining to known analytes, thereby identifying said analyte.

21. A system according to claim 20, further comprising a code for retrieving said data pertaining to known analytes from an electronic library.

22. A system according to claim 20, further comprising a code directed to updating said electronic library with said received data.

23. A system according to claim 20, further comprising a code directed to making result of execution of said code for comparing available at first location.

24. A system including memory and computer codes for analyzing data pertaining to a detected analyte, said system comprising:

a code directed to transmitting data pertaining to known analytes from an electronic library to a first location via a computer network;

a code directed to receiving said data pertaining to known analytes at said first location; and a code directed to analyzing said data pertaining to said detected analyte using said received data pertaining to known analytes at said first location and generating an analysis result.

25. A system according to claim 24, further comprising:

a code directed to receiving input from a user; and a code directed to using said input during execution of said code directed to analyzing.

26. A system including memory and computer codes for delivering analyte data, said system comprising:

a code directed to receiving a request from a user requesting data of a known analyte;

a code directed to retrieving data of said known analyte from an electronic library; and a code directed to transmitting said retrieved data to said user via a computer network.

27. A system according to claim 26, further comprising a code directed to synthesizing said known analyte using said retrieved data.

28. A system according to claim 26, further comprising:

a code directed to retrieving data of analytes which are similar to said known analyte from said electronic library;

a code directed to transmitting said retrieved data of analytes which are similar to said known analyte to said user via said computer network; and a code directed to synthesizing said analytes which are similar to said known analyte using said retrieved data thereof.

29. A system including memory and computer codes for delivering medicine to a patient at a remote location, said system comprising:

a code directed to identifying needs of said patient at said remote location;

a code directed to transmitting information relating to said needs to a processor via a computer network;

a code directed to receiving from said processor information in response to said needs; and a code directed to using information received from said processor to synthesize or dispense said medicine to satisfy said needs of said patient.

30. A system according to claim 29, wherein said code directed to identifying includes a code directed to capturing information relating to said needs using a field device.

31. A system including memory and computer codes for facilitating consumer choice, said system comprising:

a code directed to facilitating selection of a first consumer product having a known signature; and a code directed to comparing said known signature with a plurality of signatures so as to allow a similar signature indicative of a second consumer product to be selected.

32. A system according to claim 31, wherein said code directed to comparing includes:

a code directed to retrieving data pertaining to said plurality of signatures from an electronic library; and a code directed to synthesizing each of said plurality of signatures using said retrieved data so as to facilitate selection of said similar signature.

33. A system according to claim 32, wherein said code directed to selecting includes:

a code directed to retrieving data pertaining to said known signature from said electronic library; and a code directed to synthesizing said known signature using said retrieved data pertaining to said known signature.

* * * * *